US005381016A

United States Patent [19]

[11] Patent Number: 5,381,016

Moriya

[45] Date of Patent: Jan. 10, 1995

[54] METHOD AND APPARATUS FOR MEASURING PHOTOLUMINESCENCE IN CRYSTAL

[75] Inventor: Kazuo Moriya, Ageo, Japan

[73] Assignee: Mitsui Minings & Melting Co., Ltd., Japan

[21] Appl. No.: 37,994

[22] Filed: Mar. 25, 1993

[30] Foreign Application Priority Data

Mar. 30, 1992 [JP] Japan .................................. 4-074723

[51] Int. Cl.[6] .............................................. G01N 21/64

[52] U.S. Cl. ................................ 250/458.1; 250/459.1

[58] Field of Search ................ 250/458.1, 459.1, 461.1

[56] References Cited

U.S. PATENT DOCUMENTS 4,169,228 9/1979 Briska et al. .

FOREIGN PATENT DOCUMENTS 0319797 6/1989 European Pat. Off. .

OTHER PUBLICATIONS

Japanese journal of Applied Physics, vol. 22, No. 4, Apr. 1983, pp. L207–L209, Moriya et al, "Observation of Lattice Defencts in GaAs and Heat–treated Si Crystals in Infrared Light Scattering Tomography".

Applied Physics A: Solids and Surfaces A50 (1990) Jun., No. 6, Berlin, DE, Steigmeier et al, "Light Scattering Tomography and Photoluminescence Topography".

*Primary Examiner*—Paul M. Dzierzynski
*Assistant Examiner*—Richard Hanig
*Attorney, Agent, or Firm*—Dorn, McEachran, Jambor & Keating

[57] ABSTRACT

Provided are a method and an apparatus for measuring photoluminescence, which can measure the inside of crystal such as silicon. A lifetime of fluorescence-generating carrier may be evaluated in a mathematical technique without using an expensive pulse laser source. Also, an incident beam wavelength dependency and a polarization dependency of fluorescence may be evaluated by a simple method. A laser having a wavelength which can go into a crystal is projected into an object crystal, fluorescence in generated light inside the crystal is separated through a filter having a frequency band for transmission of fluorescence. An intensity and a spread of fluorescence are obtained as a function of depth from a surface of the crystal to evaluate the lifetime of luminescent center in a mathematical manner. The projection light wavelength dependency of fluorescence may be evaluated by rotating a narrow-band filter, and a polarization dependency by suitably inserting a polarizing filter into an optical patch.

22 Claims, 15 Drawing Sheets

LASER BEAM
CONDENSER SYSTEM
θ = 13~30°
β = 10°~35°
α = 16°
2
22
SURFACE OF
Si WAFER

θ =0°
θ =25.2°
θ =38.7°
100.0
90.0
80.0
70.0
60.0
50.0
40.0
30.0
20.0
10.0
0.0
TRANSMITTANCE (%)
900.00
950.00
1000.00
1050.00
1100.00
WAVELENGTH (nm)

FLUORESCENCE LIGHT IMAGE
L
L
0 msec
1 msec
3 msec

AS-GROWN CRYSTAL
FLUORESCENCE LIGHT IMAGE

CRYSTAL SURFACE

AS-GROWN CRYSTAL
SCATTERING IMAGE

IG CRYSTAL FLUORESCENCE LIGHT IMAGE

IG CRYSTAL SCATTERING IMAGE

DISTRIBUTION OF INTENSITY OF AS-GROWN CRYSTAL FLUORESCENCE LIGHT

DISTRIBUTION OF INTENSITY OF AS-GROWN CRYSTAL SCATTERING

DISTRIBUTION OF INTENSITY OF IG CRYSTAL FLUORESCENCE

DISTRIBUTION OF INTENSITY OF IG CRYSTAL SCATTERING

METHOD AND APPARATUS FOR MEASURING PHOTOLUMINESCENCE IN CRYSTAL

BACKGROUND OF THE INVENTION

1. Field of the Invention

The present invention relates to a method and an apparatus for measuring photoluminescence in crystal such as silicon.

2. Related Background Art

The photoluminescence measuring method is one of methods for measuring a distribution of defects in a crystal. When a silicon (Si) crystal is an object, an Ar (488,514 nm) laser or a He—Ne (633 nm) laser is used in the photoluminescence method. FIG. 1 shows a conventional photoluminescence measuring apparatus in which the Ar or He—Ne laser is projected toward an object and fluorescence generated in the object is spectroscopically measured through a microscope. The Ar or He—Ne laser beam is projected in the horizontal direction, then reflected at 90 degrees by a half mirror 1, and focused on an object 3 through an objective lens. The projected laser beam excites luminescent centers, which will fluoresce. The fluorescence light passes through the half mirror and forms an image through an image forming lens 11 on a pin hole or slit 5 provided on a spectroscope 4. The fluorescence light is then diffracted by a diffraction grating 6 disposed inside the spectroscope 4 to be guided onto a light receiving element 7, being distributed on the element in accordance with its frequency distribution. A control computer 8 analyzes the image received by the light receiving element while controlling a stage controller 9 to move the object 3 two-dimensionally, so as to show a distribution of generated fluorescence on a display.

It is important to measure a life time of luminescence center in the photoluminescence method. A general measurement of life time is such that a projection beam is supplied from a pulse laser source or pulse light source and that a damping of fluorescence produced under irradiation with the pulse beam is evaluated, as shown in FIG. 2. There is another method for measuring the life time, in which a semiconductor laser beam is input as excitation energy and a damping of exciton is observed by microwave.

There are other conventional techniques concerning the photoluminescence method for example as described in Japanese Patent Application No. 54-109488 and Japanese Laid-open Patent Application No. 62-119446, in which a scattering image or a fluorescence image of defect is obtained using a laser beam. Also, Japanese Patent Application No. 60-53368 describes a method to obtain a scattering image of defect in silicon crystal under irradiation with YAG laser. Additionally, reference is made to K. Moriya and T. Ogawa, Jpn. J. Appl. Phys., 22 (1983)L207 describing related art.

SUMMARY OF THE INVENTION

As described above, the photoluminescence measurement for example of silicon is carried out under irradiation with the Ar or He—Ne laser in the conventional methods. The laser beams used, however, have relatively short wavelengths, which cannot fully penetrate a crystal. Thus, the measurement was limited only to the vicinity of a crystal surface (about 1–2 μm to the surface). Further, surface recombination centers are produced near the surface of crystal, which differ a structure of surface from an intrinsic internal structure of crystal. An accurate measurement of physical properties of inner crystal cannot be expected by the conventional techniques, which only allow the measurement near the surface. In addition, since a silicon crystal is usually subjected to the IG (intrinsic gettering) treatment, it has a distribution of defects in the direction of depth of wafer. Even if the crystal should be cleaved to observe a surface thus cleaved in order to measure the distribution of defects in depth, an accurate measurement would be impossible due to an influence of the cleaved surface.

It is, therefore, a first object of the present invention to provide a method and an apparatus for measuring the photoluminescence, enabling a measurement of inner crystal.

As described above, the measurement of life time of luminescent center is normally conducted by projecting a pulse laser toward an object and observing a time dependence of fluorescence. A measuring system using the pulse laser is, however, complicated and expensive. Further, the fluorescence is extremely dark when it is generated by excitation light, which is rarely absorbed but, therefore, can reach the inner crystal. Thus, in order to obtain fluorescence with measurable intensity, the pulse laser used must have a high peak value (energy strength), which could give a damage on the crystal itself.

It is a second object of the present invention to provide an apparatus enabling a measurement of life time without using a pulse laser source.

Further, a wavelength-dispersing spectroscope is employed as an observation optical system as shown in FIG. 1 in the conventional methods. Such a spectroscope is dark and unsuitable for measurement of weak fluorescence. The optical system is also expensive and large in scale.

It is another object of the present invention to provide a photoluminescence measuring apparatus enabling the measurement of photoluminescence through a simple optical system without using a spectroscope.

The fluorescence produced in a silicon crystal is very weak, and, therefore, a fluorescence intensity would be extremely low with a laser having a wavelength in a range of 800–1500 nm, which has a small absorption coefficient but a high transmittance enough to reach the inner crystal. Moreover, the fluorescence produced by excitation with the laser beam having a wavelength in the above range has a wavelength of 0.9–2 μm, which is partially overlapped with a wavelength range of scattered light of the projected laser.

It is, therefore, still another object of the present invention to provide a photoluminescence apparatus which can evaluate weak fluorescence while separating it from scattered light of a projected laser beam.

For example, the silicon has two peaks of fluorescence between 900 nm and 1300 nm and between 1400 nm and 1800 nm, which are different from each other in fluorescing mechanism. The two fluorescences may have an interaction, which raises a necessity to examine a wavelength dependency thereof while changing a wavelength of incident beam. Similarly, the scattered light and the fluorescence light respectively have a specific polarization dependency, and, therefore, it becomes important to study the polarization dependency.

It is, therefore, still another object of the present invention to provide a method and an apparatus for measuring photoluminescence, which can evaluate the incident light wavelength dependency and the polarization dependency of produced fluorescence in a simple arrangement.

In the present invention, achieving the above objects, a laser beam having a wavelength which an object crystal can transmit is focused into a diameter of several microns to irradiate the crystal, and light produced inside the crystal is made to pass through a narrow-band transmission filter, whereby only excitation fluorescence is separated from the others, then to be observed. It is preferable in case of the silicon crystal that the wavelength of the projected laser beam be 800–1500 nm. A laser beam having a wavelength in the range may fully penetrate the crystal.

The thus-obtained fluorescence may be visualized by using an image pickup device, so that appearance of fluorescence may be observed at a specific position in the crystal.

The life time of fluorescence-producing exciton is determined by obtaining a fluorescence intensity (I) and an expanse or spread (L) of fluorescence image as a function of penetration depth of the laser beam into the crystal from the thus-obtained two-dimensional image on the basis of a two-dimensional image generated inside the crystal under the condition that a thin focused laser is projected inside the crystal.

When a polarizing filter is inserted into a laser beam projection optical system or into a light receiving optical system, the polarization dependency of fluorescence may be known. Also, when an interference filter is used to change a center wavelength of transmitted light, the wavelength dependency of fluorescence may be known.

DESCRIPTION OF THE EMBODIMENTS

Figure 1:
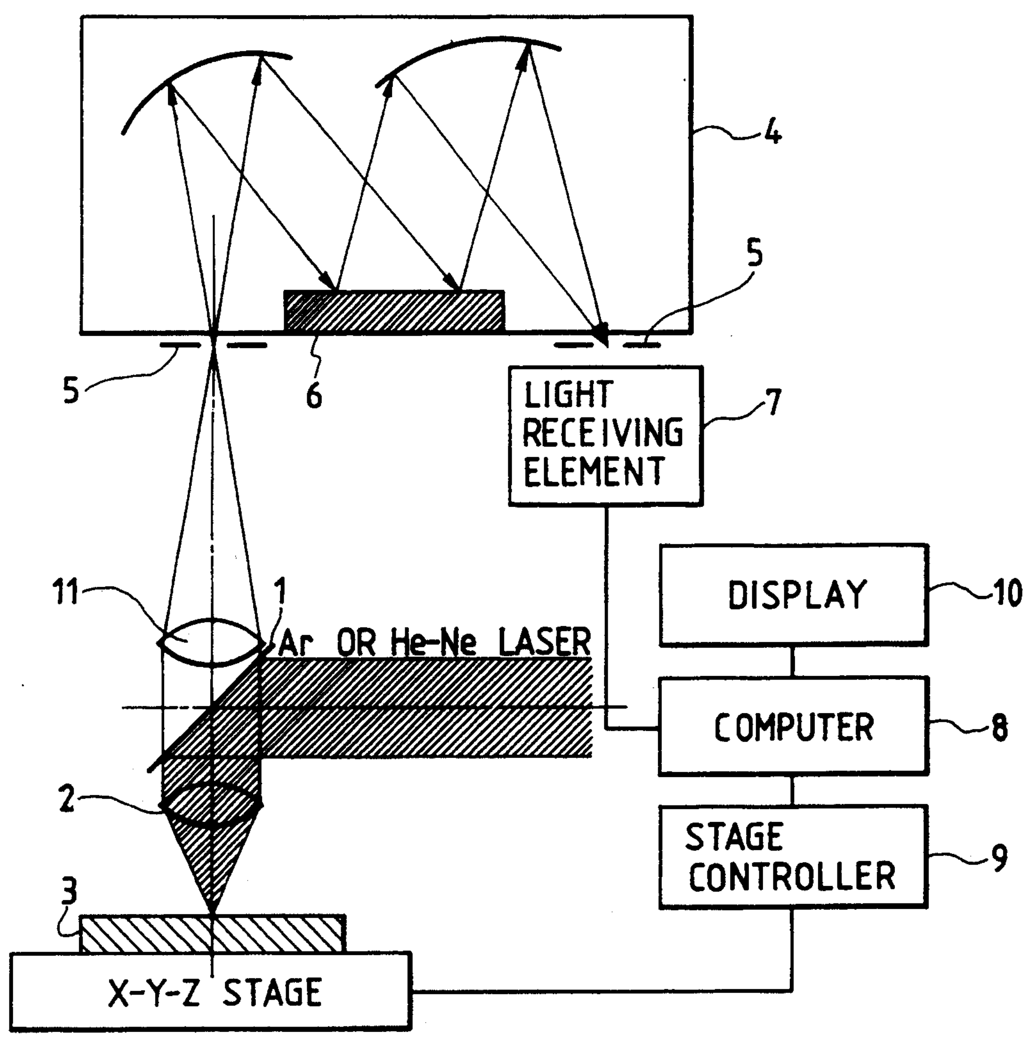
FIG. 1 is a drawing to show a conventional fluorescence observing apparatus.
Figure 2:
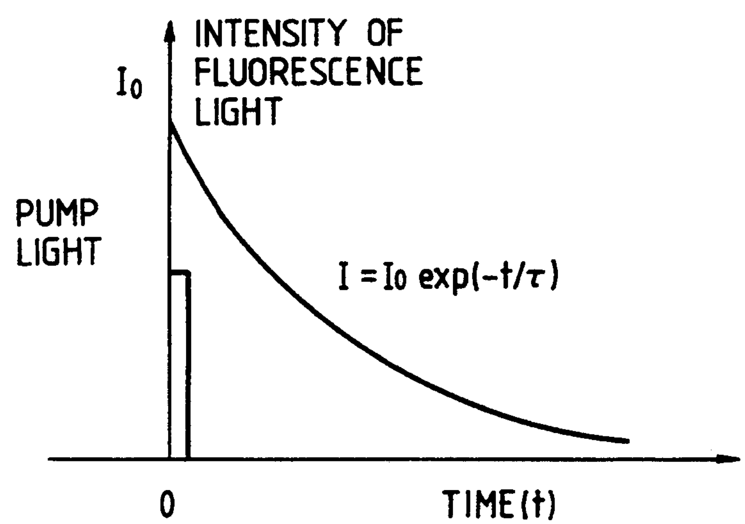
FIG. 2 is an explanatory drawing to show a life time of fluorescence produced with a pulse laser.
Figure 3:
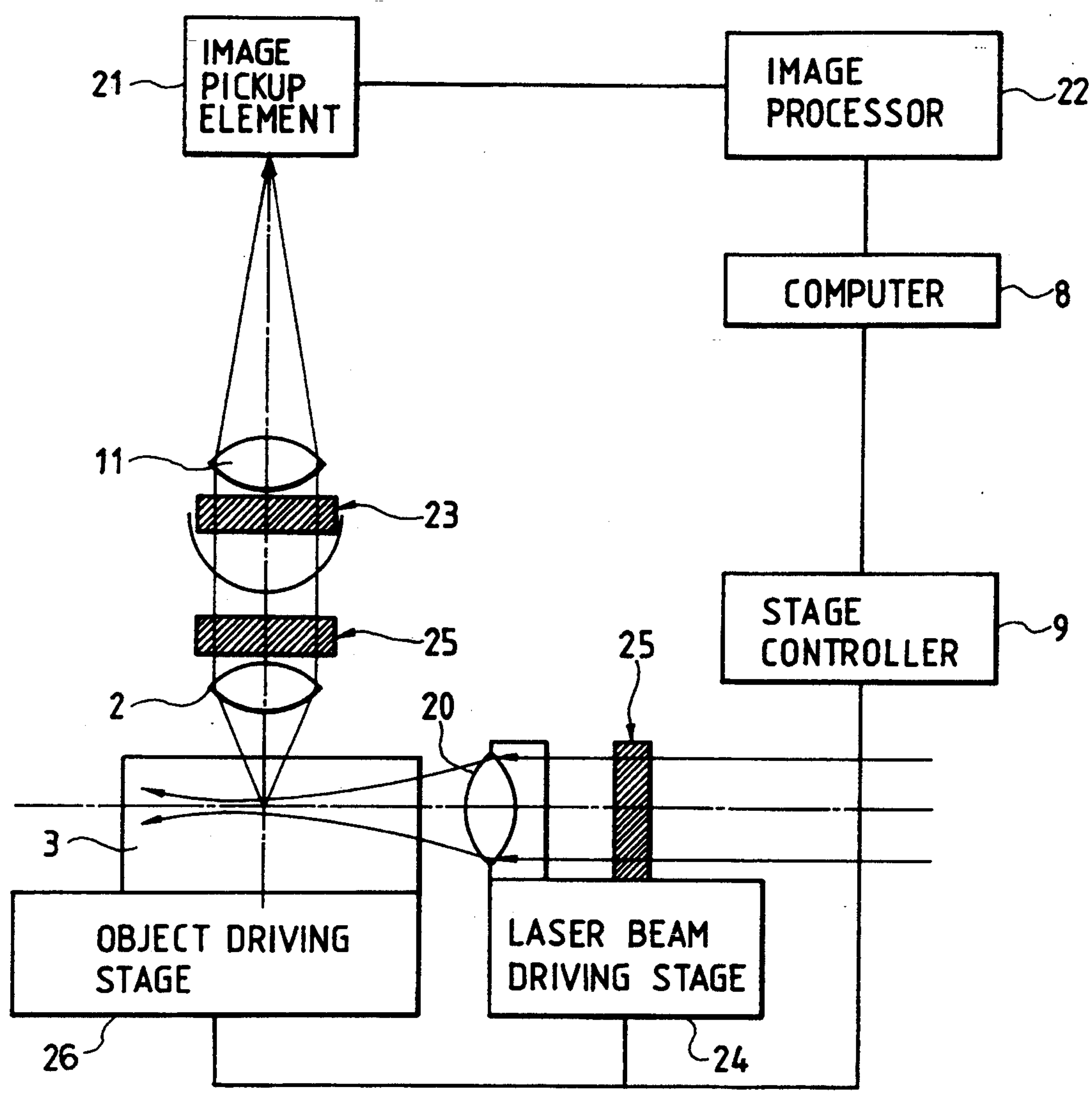
FIG. 3 is an explanatory drawing to illustrate a first embodiment of an apparatus according to the present invention.

Fig. 3 shows a first embodiment according to the present invention. Silicon is supposed to be a crystal as an object in the following description.

A laser beam with a wavelength of 800–1500 nm is projected through a condenser lens 20 and then through a polished face of a silicon crystal 3 into the crystal. The condenser lens 20 condenses the laser beam into diameter of 3–20 $\mu$m. Light generated in the crystal passes through an objective lens 2 and an image forming lens 11 to form an image on an image pickup device 21. Image information picked up by the image pickup device is processed by an image processor 22, and necessary information is transferred to a control computer 8.

Numeral 23 designates a transmission filter inserted into a light receiving optical system composed of the objective lens 2, the image forming lens 11, and the image pickup device 21. The filter has a narrow band characteristic to separate out from the scattered light and to transmit only fluorescence generated by carriers excited with the projected laser beam in the silicon crystal. Since the generated fluorescence has a wavelength of 0.9–2 microns in case of silicon, the filter is required to have the transmission property only in this band.

Numeral 9 denotes a stage controller for controlling a laser beam driving stage 24 for changing a projection position of the projected laser or an object driving stage 26 for moving an object. The stage controller 9 properly controls a relative position between the laser beam source and the object to observe a state of fluorescence two-dimensionally, and two-dimensional image pickup information is analyzed from the thus-obtained image information.

Numeral 25 denotes polarizing elements for polarizing the projected laser beam or the scattered light to be received. The polarizing elements may be inserted into an optical path with necessity and rotated to obtain a desired polarization state, whereby the polarization dependency of fluorescence thus produced may be observed. If the polarizing elements are adjusted to attain the minimum scattering intensity, weak fluorescence becomes easy to be detected. In the example of FIG. 3, the scattering intensity of micro precipitates (diameter$<\lambda/10$) may be minimized when the polarization direction (electric field direction) is parallel to the sheet plane of the drawing. The polarization dependency of scattered light is different from that of fluorescence. In general, the scattered light has a strong direction dependency, while the fluorescence a weak dependency. Accordingly, the polarization direction is set as to weaken the scattering when the fluorescence is observed, while the polarization direction is set as to increase the scattering when the scattered light is observed, whereby suitable measurements may be carried out.

Figure 7:
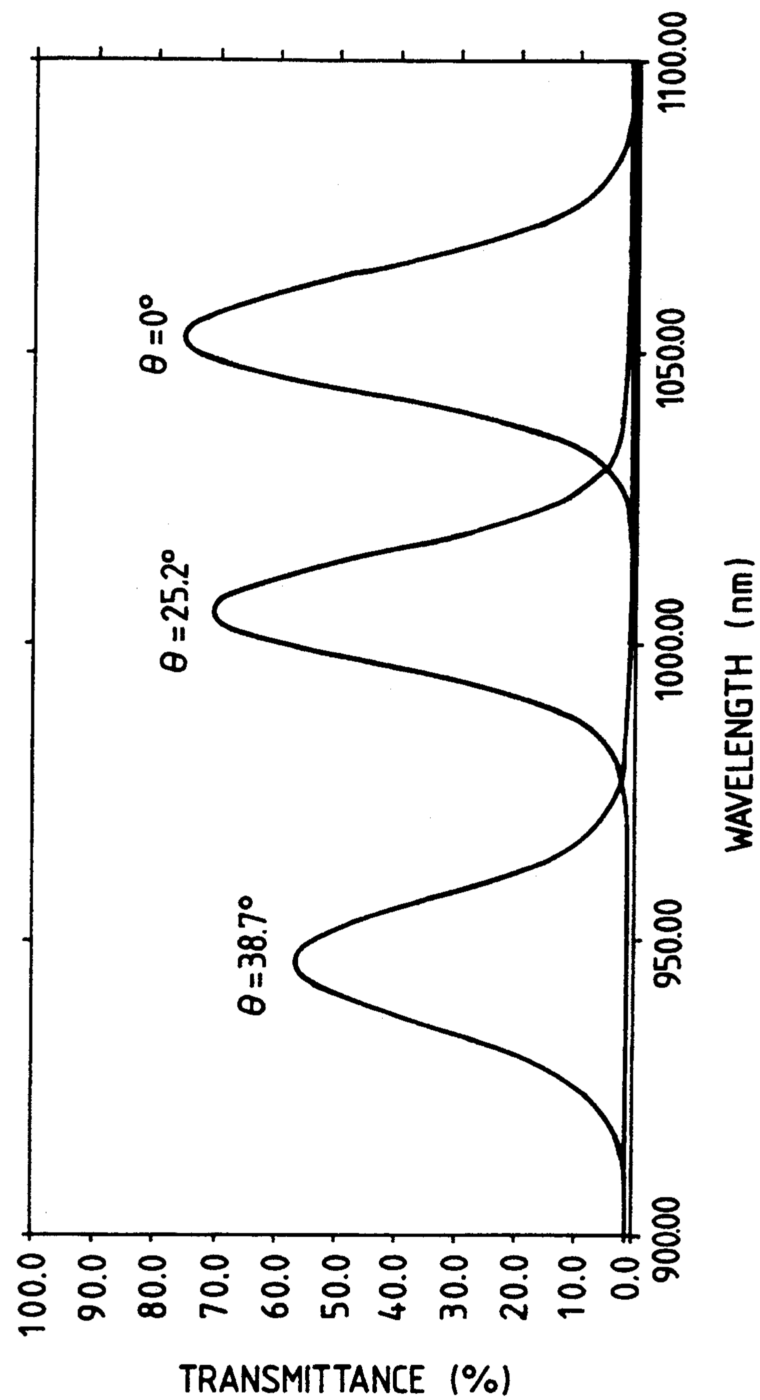
FIG. 7 is a drawing to show a change of transmission center wavelength when a filter is inclined.
Figure 8:
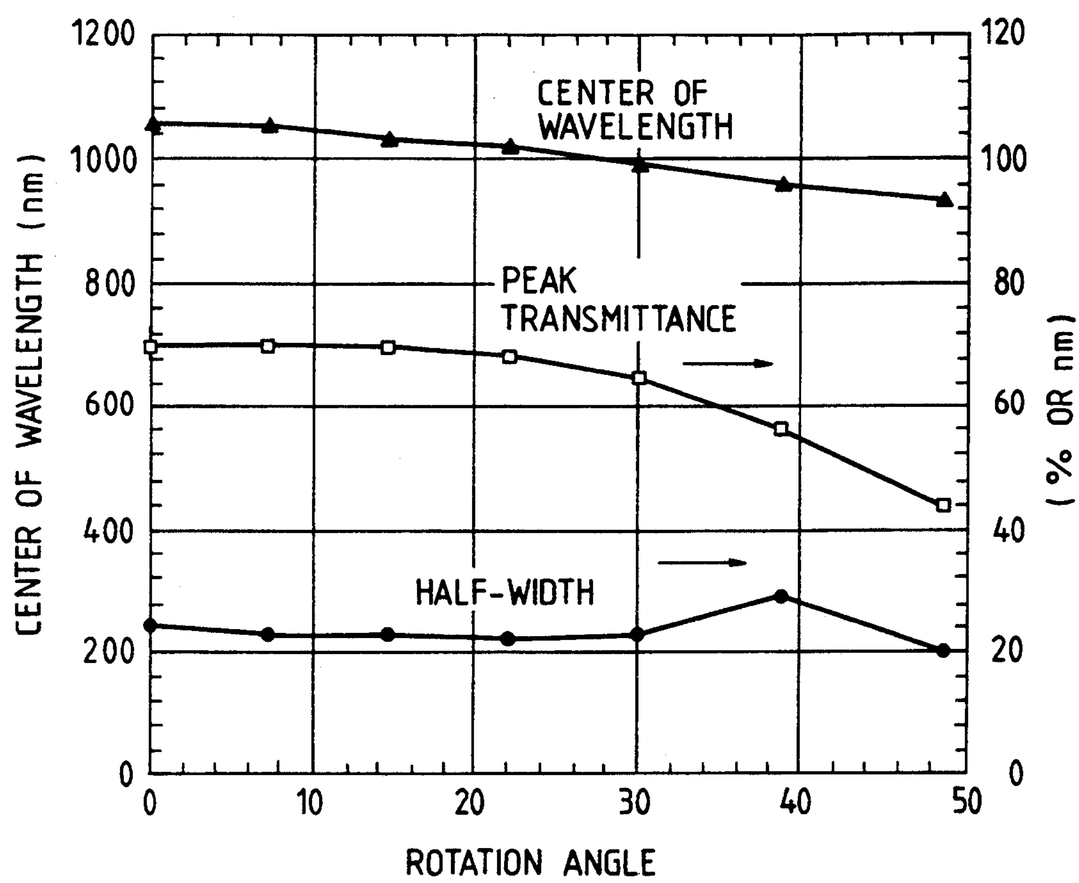
FIG. 8 is a drawing to show correlations of a center wavelength, a peak transmittance, and a half-width with respect to a rotation angle of the filter.

A surface of the band transmission filter 23 is normally coated by an interference film. Then, if the filter is properly rotated, an apparent interference film thickness varies thereby to make the transmission center wavelength variable. Thus, changing an angle between the filter surface and the optical axis, the transmission center wavelength may be varied, which allows the observation of the wavelength dependency of fluorescence generation. If the objective lens is of an infinity-corrected type, a parallel beam may be obtained between the objective lens and the image forming lens, which is convenient for insertion of the interference filter. A shift of image does not occur when the interference filter is inclined. FIG. 7 is a drawing to show a change of the center wavelength of transmitted light when the interference filter 23 is inclined with respect to the optical axis, and FIG. 8 is a drawing to show changes of peak transmittance and half-width when the center wavelength is varied. The wavelength dependency of fluorescence can be of course readily measured as well by using a wavelength variable laser.

A measurement of the wavelength dependency of fluorescence in a semiconductor is effective to study a deep level structure in a band of crystal.

Figure 4:
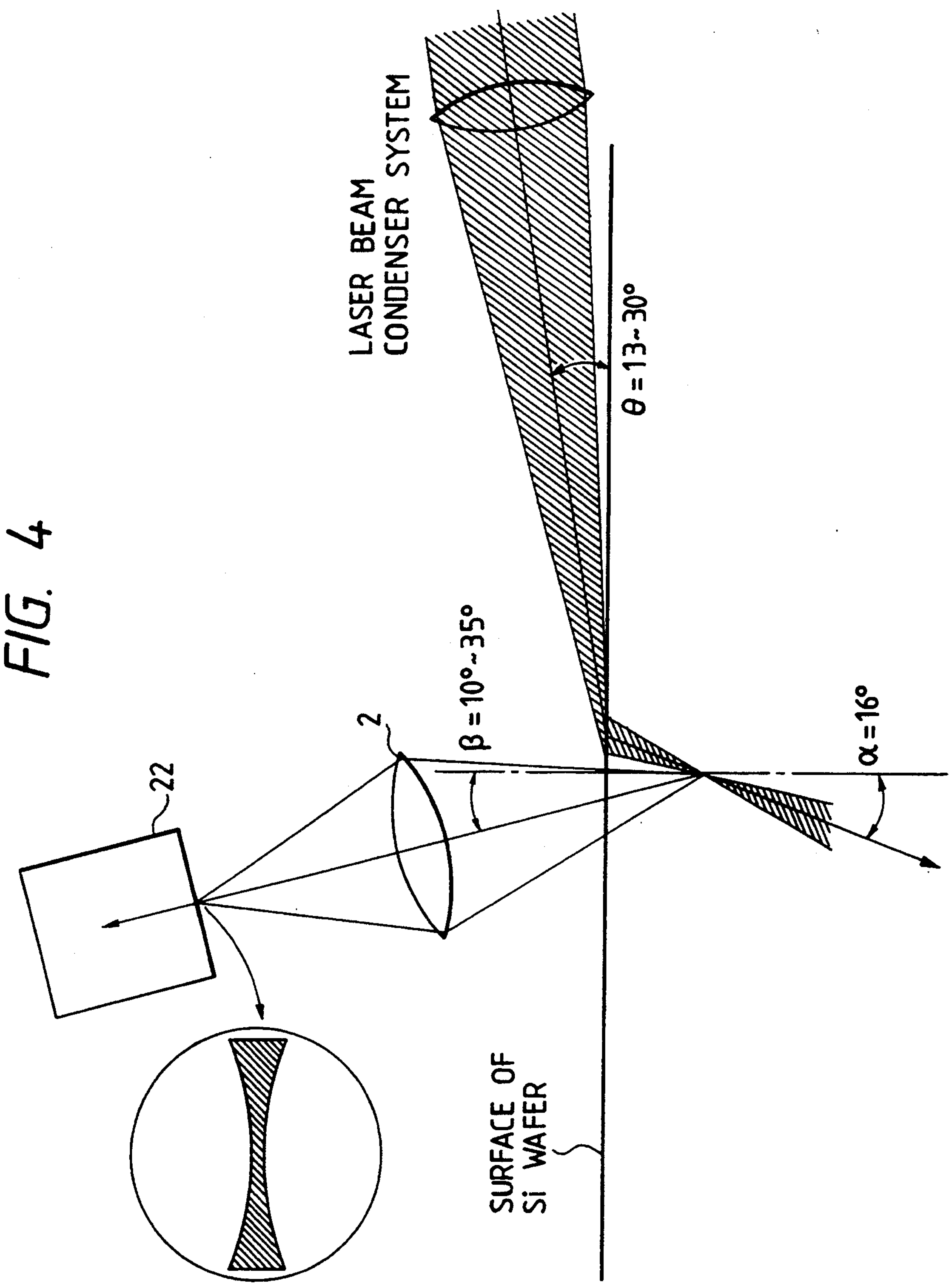
FIG. 4 is an explanatory drawing to illustrate a second embodiment of the present invention.

FIG. 4 shows a second embodiment according to the present invention. The observation is performed in the direction perpendicular to the incident plane of the laser beam in the first embodiment as shown in FIG. 3, while the observation is done on the same plane as the incident plane in the second embodiment. The laser beam is incident at an incident angle of 60–77 degrees ($\theta=13$–$30$ degrees) into the surface of crystal. The incident laser beam is refracted at the crystal surface to enter the inside of crystal at an angle of refraction ($\alpha$) of about 16 degrees. Since a part of the incident laser beam is reflected at the crystal surface, the observation should be carried out in such a direction ($\beta=10$–$35$ degrees) that the reflected light does not enter the light receiving element 22.

Figure 5:
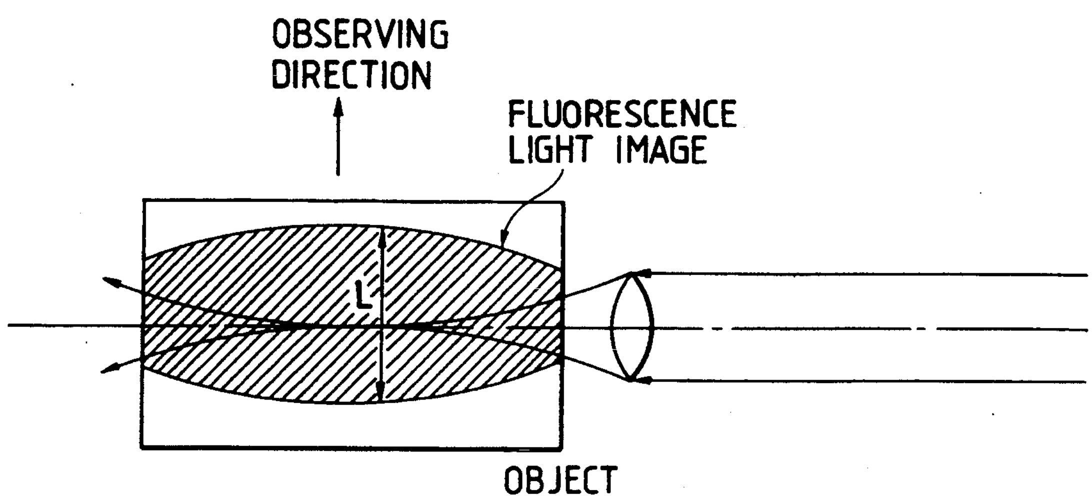
FIG. 5 is a schematic drawing to illustrate a state of fluorescence produced.
Figure 6:
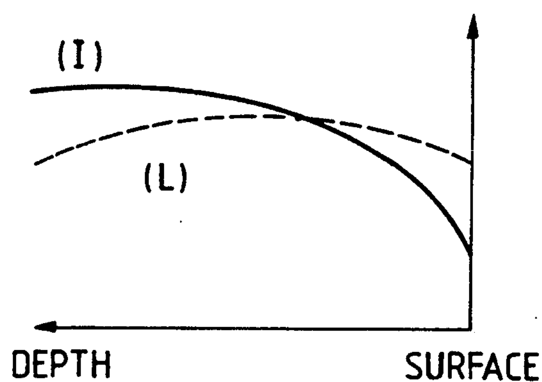
FIG. 6 is a drawing to illustrate a correlation between a spread and an intensity in a fluorescence image.

FIG. 5 is a drawing to schematically show a state of fluorescence generation when the object is irradiated with the excitation laser. FIG. 6 is a drawing to show a spread (L) of generated fluorescence and an intensity (I) of fluorescence with respect to a penetration depth of the laser beam from the object surface on the horizontal axis. Obtaining L and I as a function of depth from the crystal surface, the life time of excitation carrier may be evaluated as a function of depth. The spread (L) of fluorescence image is calculated at a position where the fluorescence intensity becomes 1/e.

Generally, a diffusion coefficient of excited carrier is expressed as follows from the Einstein relation.

$$D_n=\mu_e k_B T/q;\ D_p=\mu_p k_B T/q,$$

where $k_B$ is the Boltzmann constant, T a temperature, q a charge, $\mu_e$ a mobility of electron, and $\mu_p$ a mobility of hole.

Also, a recombination life time ($\tau$) of minority carrier is given by the following equation.

$$\tau^{-1}=Nr\cdot S\cdot V_{th},$$

where Nr is a density of recombination center, S a capture cross section, and $V_{th}$ a thermal velocity of minority carrier.

Consequently, an existential probability is as follows if an excited minority carrier moves by a distance R:

$$\mathrm{EXP}(-R/M).$$

There is the following relation between a diffusion length (M) of carrier and the recombination life time ($\tau$).

$$M=\sqrt{D_n\tau}$$

Thus, if the spread (L) of the fluorescence intensity distribution can be measured, the diffusion length (M) of carrier may be obtained. Namely, the position where the fluorescence intensity becomes corresponds to M.

Figure 9:
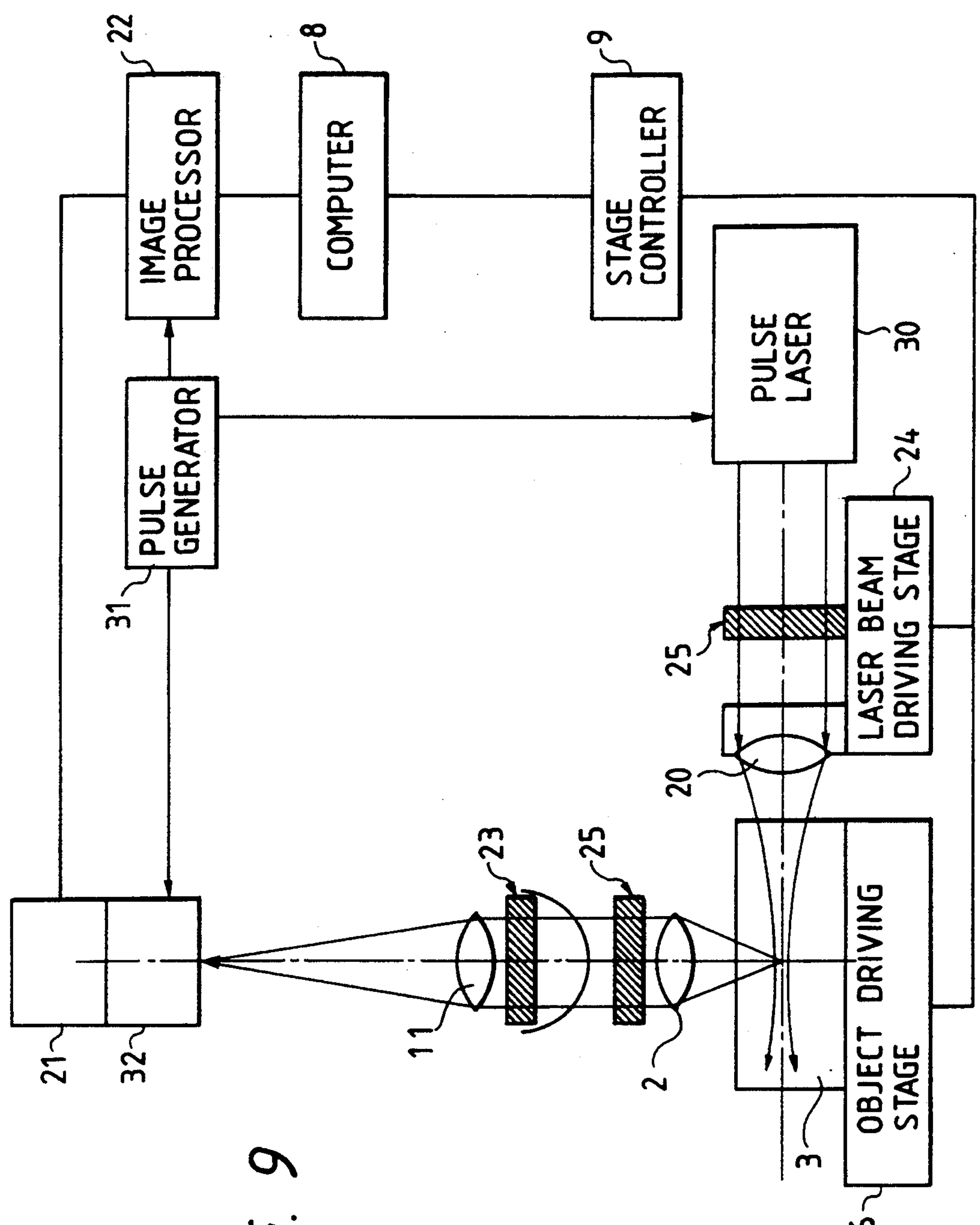
FIG. 9 is an explanatory drawing to illustrate a third embodiment of the present invention.

According to the present invention, the life time of exciton may be analyzed by the mathematical technique with a continuous wave laser as described above. Also using a pulse laser, the spread of fluorescence image and the life time of carrier may be more accurately measured. FIG. 9 shows a third embodiment according to the present invention, which employs such a pulse laser as a light source.

A pulse laser source 30 emits a beam by a trigger signal generated by a pulse generator 31. A time dependency of fluorescence produced is measured by a gated image amplifier 32. In detail, after light emission of pulse laser, a gate is opened for a short time at a delay of predetermined time (t), and the measurement is repeated several times while changing the time t, whereby the generation of fluorescence may be observed with time.

Figure 10:
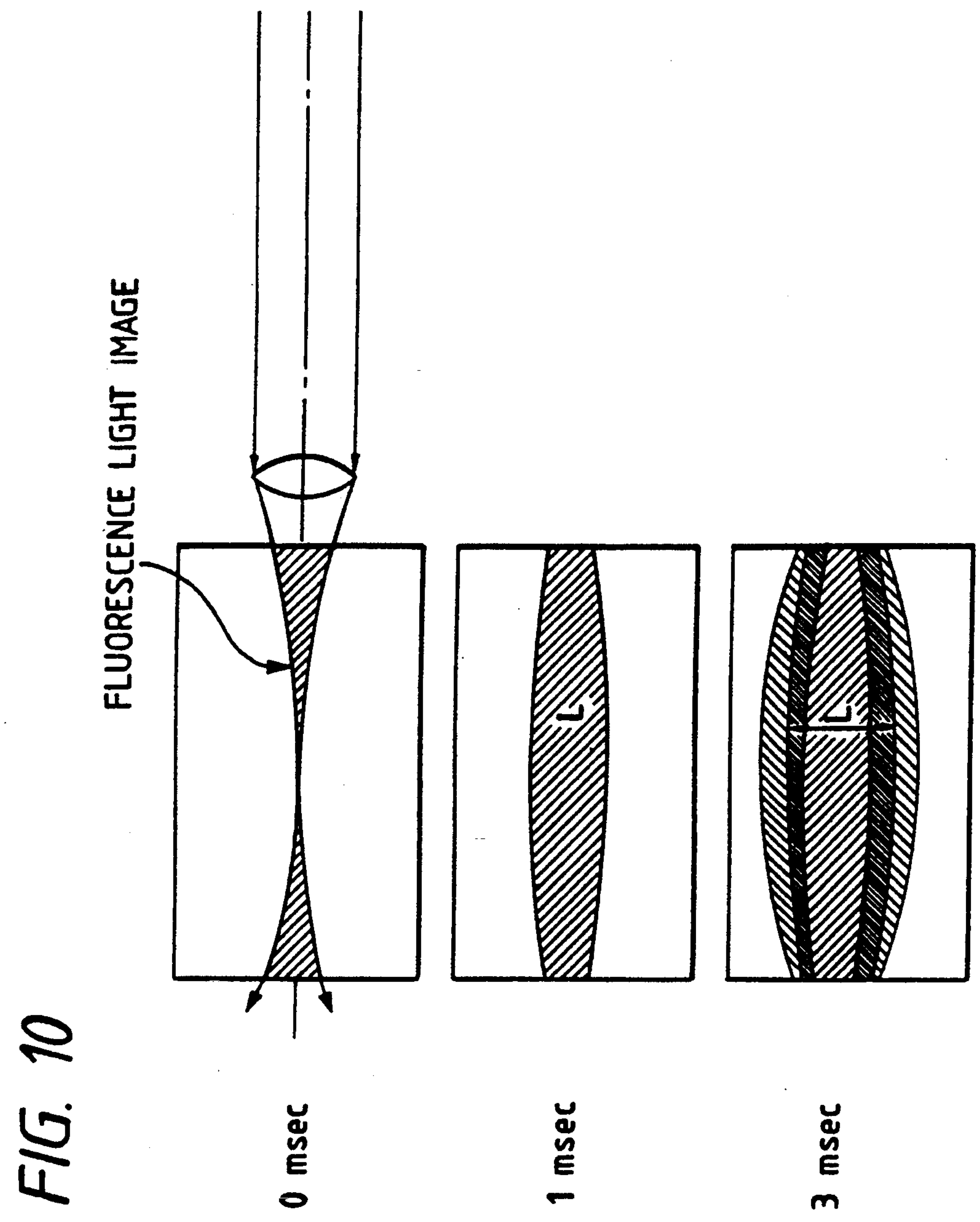
FIG. 10 is a drawing to show a change of produced fluorescence with time.
Figure 11:
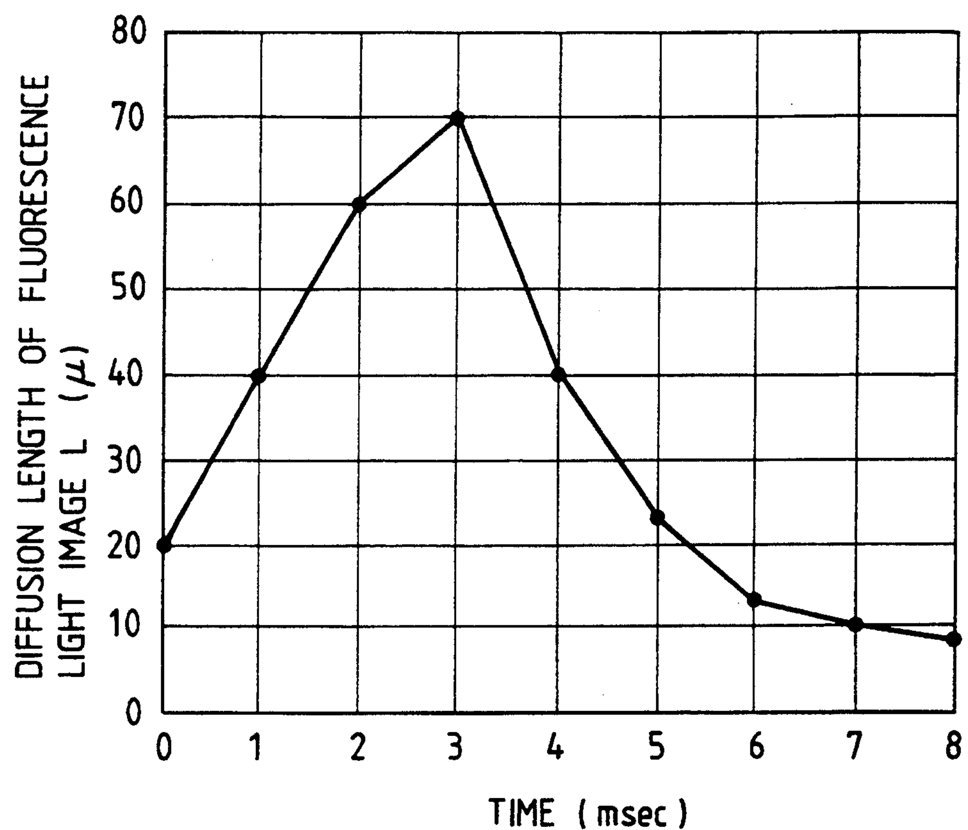
FIG. 11 is a graph to show a change of spread of fluorescence image with time.
Figure 12A:
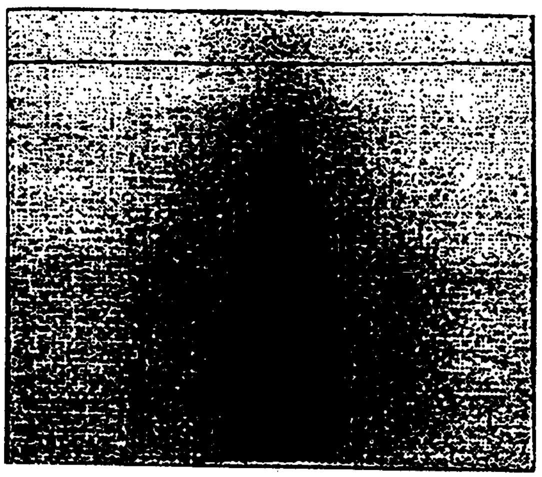
FIG. 12A to FIG. 12D are drawings to respectively show a correlation between an fluorescence image and a scattering image.
Figure 12B:
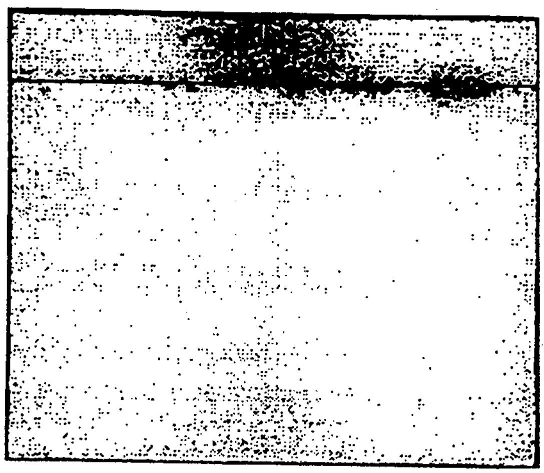
Figure 12C:
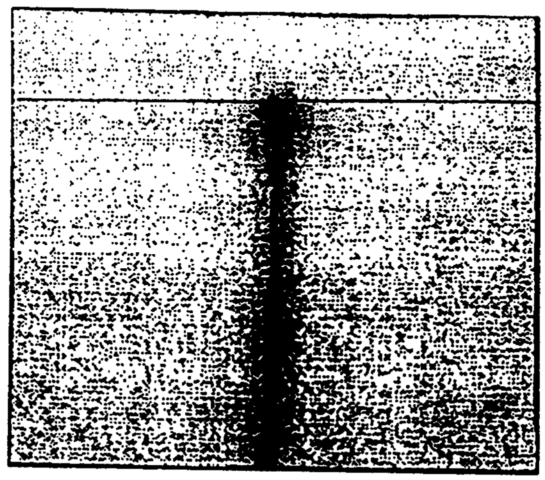
Figure 12D:
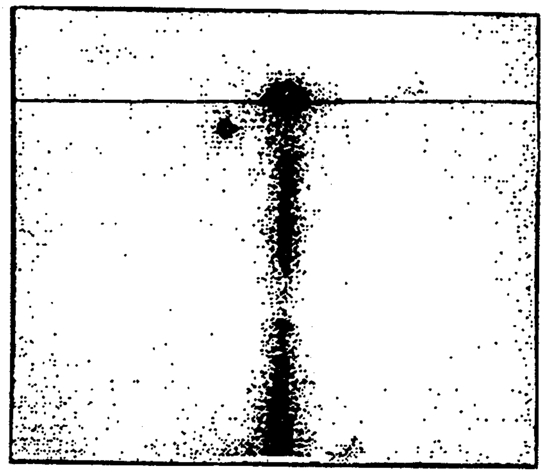
Figure 13A:
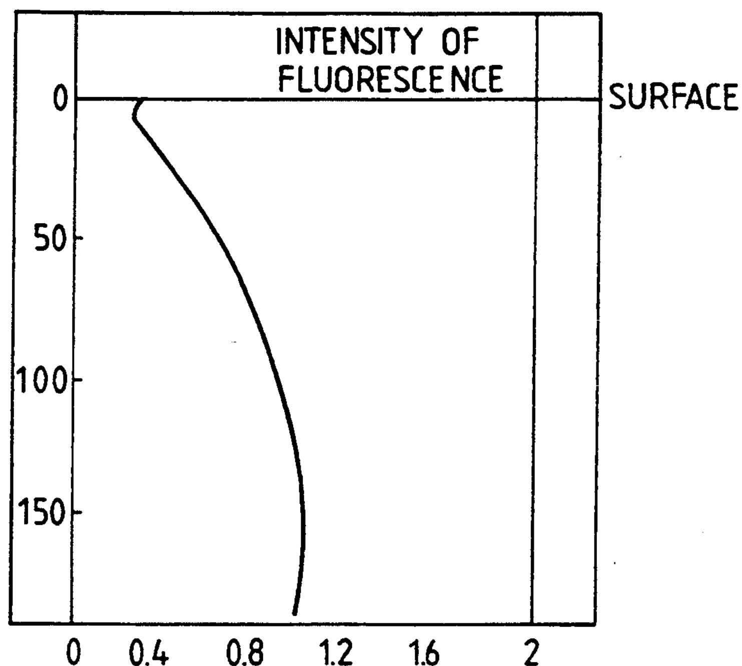
FIG. 13A to FIG. 13D are graphs to respectively show an intensity distribution in a fluorescence image or in a scattering image.
Figure 13B:
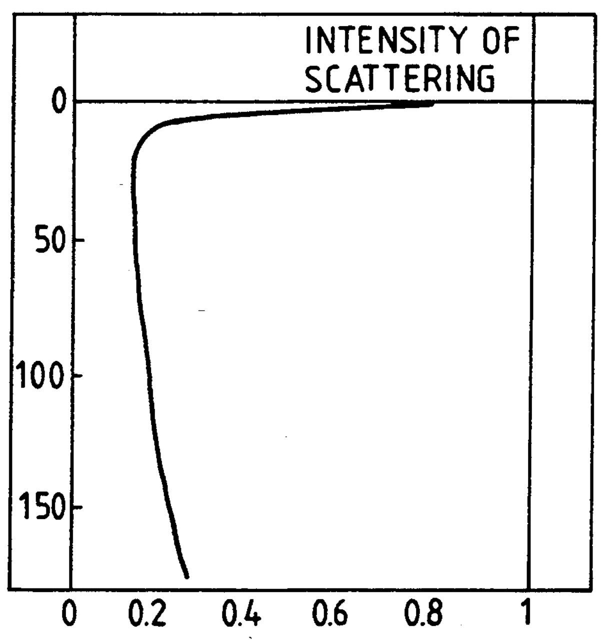
Figure 13C:
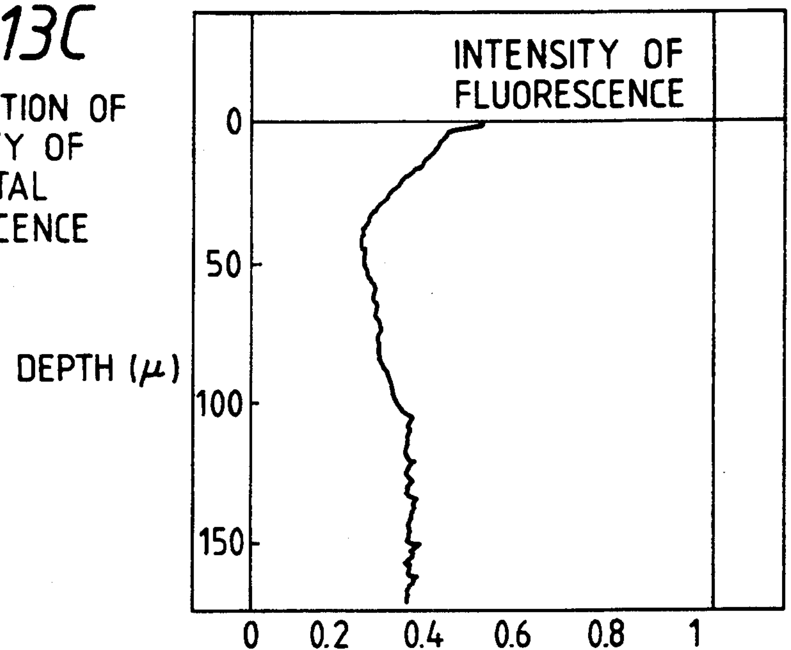
Figure 13D:
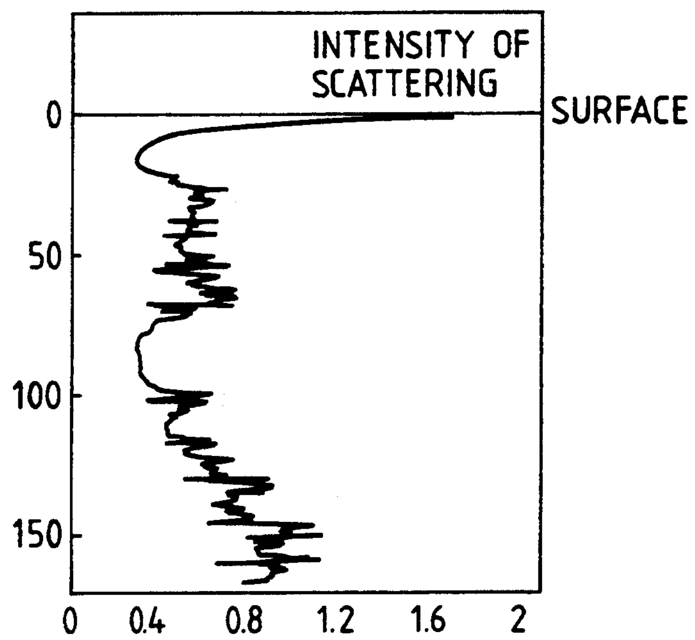

FIG. 10 is a drawing to show a state of generation of excitation fluorescence image when a pulse laser is projected into an object for a certain time by the apparatus as shown in FIG. 9, and FIG. 11 is a graph to show a change of spread (L) of fluorescence image with time. The recombination life time ($\tau$) may be accurately measured from FIG. 11.

FIGS. 12A–12D to FIG. 15 show results of experiment, in which the inside of silicon crystal was observed by the apparatus according to the present invention.

A CW YAG laser with a wavelength 1.064 $\mu$m and an intensity 400 mW, fully condensed (into diameter of about 2–4 $\mu$m), was guided to enter a polished surface of Si crystal to excite luminescent centers, and scattered light and fluorescence light generated were observed through filters with center wavelength 1064 nm and 950 nm, respectively, and with half-width 20 nm on a cleaved surface. The laser beam was made to go into a depth of about 100 $\mu$m from the surface, preventing fluorescence inside the crystal from being trapped by the surface.

Figure 14A:
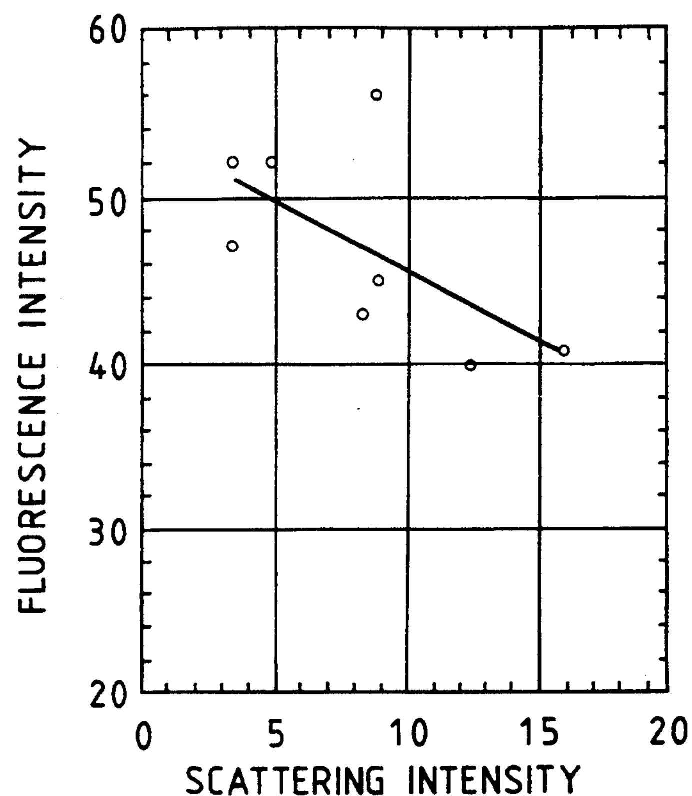
FIG. 14A and FIG. 14B are graphs to respectively show a correlation between a scattered light intensity and a fluorescence image.
Figure 14B:
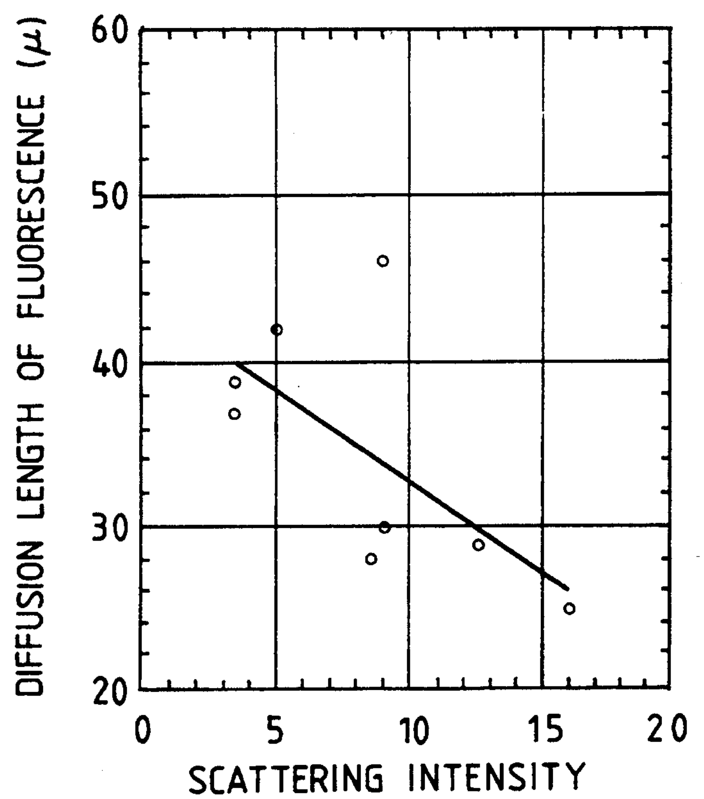

Samples were a wafer subjected to the IG treatment, which had many defects, and an As-grown wafer rarely having a defect. FIGS. 12A to 12D show a correlation between a fluorescence image and a scattering image. It is seen that the defectless As-grown wafer has a wide spread of fluorescence image. FIGS. 13A to 13D show intensity distributions in fluorescence image and in scattered image as a function of depth. FIG. 14A is a graph to show a relation between a scattering intensity and a fluorescence intensity, and FIG. 14B is a graph to show a relation between a scattering intensity and a spread of fluorescence image. It is seen that there is an inverse correlation between the intensity of scattered light and the spread width of fluorescence image. Thus, according to the present invention, the influence of defects inside the crystal on the diffusion length (M) of carrier may be quantitatively known as a function of depth from the crystal surface. Accordingly, it becomes possible to evaluate how to reduce the influence of defects on the movement of carriers in the crystal surface while arranging a distribution of defects (IG treatment) created inside the crystal.

Figure 15:
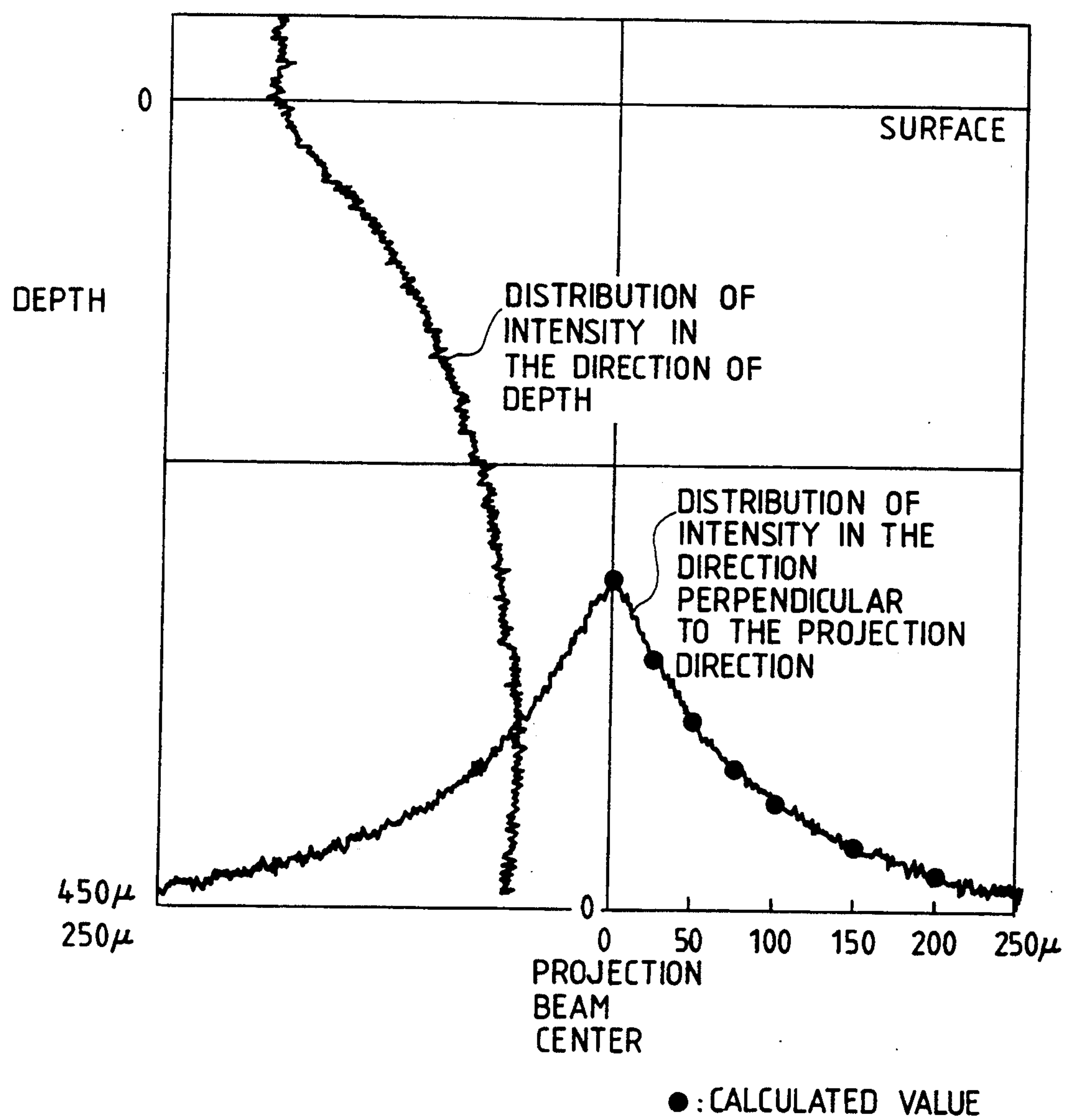
FIG. 15 is a drawing to show a relation between measured values and calculated values in an experiment of fluorescence intensity.

FIG. 15 shows fluorescence intensity distributions measured along the direction of depth and along a direction perpendicular thereto. In FIG. 15 dots represent calculated values obtained by the above-described calculation with the carrier diffusion length (M) of 85 μm. It is seen that the calculated values show good coincidence with the measured values.

As shown in FIG. 15, the intensity distribution decreases the intensity along the depth toward the crystal surface. This is because the excited carriers produced by the laser are absorbed (recombined) in the surface. The density of recombination center near the surface may be thus measured by obtaining the distribution.

The present invention was described based on the preferred embodiments, and it is needless to mention that the present invention should not be limited to the embodiments as described above. Specifically, although the object crystal was the silicon crystal in the above examples, it should be noted that the present invention can be applied to other various object crystals, for example GaAs, InP, with suitable selection of wavelength of projected laser beam and transmission wavelength band of the band filter. Also, the narrow-band filter may be a band pass filter having a narrow transmission light band such as an interference filter, or a variable filter such as a spectroscope. Further, the narrow-band filter may be an etalon having an adjustable gap. The filter may be replaced by a notch filter having a transmittance of zero near the laser wavelength, as well as the band pass filter.

According to the present invention, the photoluminescence intensity distribution may be measured in a crystal in the simple arrangement as described. Since the laser beam can penetrate a sufficient depth in the crystal, the fluorescence in the original inner crystal may be measured without influence of recombination centers in the crystal surface. Further, the fluorescence life has a close relation with the life time of carrier, which is an important measuring element. According to the present invention, the life time can be presumed in the mathematical technique from the distribution of measured fluorescence. The damping time of fluorescence intensity can be directly measured with the projection light of pulse laser, which enables the more accurate measurement.

A dangling bond is formed in the surface of silicon crystal without an oxide layer being provided thereon, which could become an absorption (recombination) center. Thus, the measurement of life time is normally carried out after an oxide film is formed on the surface, in the conventional methods. In the method according to the present invention, the diffusion may be analyzed without formation of such an oxide film on the surface, whereby the density of recombination center ill the surface and the diffusion distance inside the crystal may be accurately separately measured. The formation of such an oxide film requires a heat treatment at a high temperature (at about 900° C.). An electric oven for the heat treatment could become a contamination source, which could greatly change the life time of sample.

What is claimed is:

1. A photoluminescence measuring apparatus comprising:

- a laser source for emitting a laser beam having a wavelength which can go into the inside of an object crystal;
- a projection optical system for condensing the laser beam into a predetermined diameter then to project it toward the inside of crystal;
- a light receiving optical system for receiving light generated in the crystal with the projected laser beam;
- a filter disposed in said light receiving optical system and having a band transmission characteristic to allow only fluorescence in said generated light to pass therethrough; and
- a processor for evaluating the fluorescence having passed through said filter to analyze an internal structure of the crystal.

2. A photoluminescence measuring apparatus according to claim 1, wherein said processor measures a spread and an intensity of image of generated fluorescence along a depth from the surface of the crystal to evaluate an average movement distance of carrier as a function of depth.

3. A photoluminescence measuring apparatus according to claim 2, wherein said processor forms an image of scattered light and an image of fluorescence generated with the incident laser beam to evaluate a correlation between the intensity or the spread of fluorescence, and the scattering intensity.

4. A photoluminescence measuring apparatus according to claim 3, wherein said processor has driving means for moving said laser source or the object crystal to a predetermined position, whereby said processor observes the intensity of said fluorescence or the spread of the image of fluorescence two-dimensionally while suitably moving said laser source or the object crystal through the driving means.

5. A photoluminescence measuring apparatus according to claim 4, wherein a correlation is evaluated between a two-dimensional image of scattered light in the crystal having the same wavelength as said projected laser beam and a two-dimensional image of intensity and distribution of fluorescence.

6. A photoluminescence measuring apparatus according to claim 5, wherein said laser source is a wavelength variable laser arbitrarily continuously variable in a predetermined wavelength range, and wherein an incident beam wavelength dependency of the scattering image or the fluorescence image is measured while suitably changing the wavelength.

7. A photoluminescence measuring apparatus according to claim 1, wherein said projection optical system and/or the light receiving optical system are provided with polarizing means, and wherein a polarization dependency of the scattering image or the fluorescence image is measured by changing a polarization direction of the projected laser beam and/or a polarization direction of the scattered light or the fluorescence.

8. A photoluminescence measuring apparatus according to claim 7, wherein said band transmission filter is inclined to change the transmission center wavelength of the projected laser beam, whereby a wavelength dependency of the scattering image or the fluorescence image is measured.

9. A photoluminescence measuring apparatus according to claim 8, wherein a pulse laser is used as said laser source, and wherein a time dependency of the fluorescence image is measured by measuring the fluorescence generated with the pulse laser with time.

10. A photoluminescence measuring apparatus according to claim 1, wherein said object crystal is a silicon crystal.

11. A photoluminescence measuring apparatus according to claim 10, wherein the wavelength of said projected laser beam is 800 to 1500 nm, and the wavelength of the fluorescence image generated is 0.9 to 2 μm.

12. A photoluminescence measuring method comprising:

projecting a laser beam having a wavelength which can go into a crystal, into the object crystal while condensing the laser beam into a predetermined diameter;

receiving light generated in the crystal with the projected laser beam;

allowing only fluorescence in the light, generated by exciton in the crystal, to pass through a filter; and evaluating said fluorescence to analyze an internal structure of the crystal thereby.

13. A photoluminescence measuring method according to claim 12, wherein a spread and an intensity of said fluorescence image are measured along a depth from a surface of the crystal, to evaluate an average movement distance of carrier as a function of depth in the crystal.

14. A photoluminescence measuring method according to claim 13, wherein images of said scattered light and fluorescence are formed to evaluate a correlation between the intensity or the spread of the fluorescence, and the scattering intensity.

15. A photoluminescence measuring method according to claim 14, wherein said projected laser beam or the object crystal is suitably moved to observe the fluorescence intensity of the fluorescence or the spread of the fluorescence image two-dimensionally.

16. A photoluminescence measuring method according to claim 15, wherein a correlation is evaluated between a two-dimensional image of scattered light in the crystal having the same wavelength as said projected laser beam and a two-dimensional image of intensity and distribution of the fluorescence.

17. A photoluminescence measuring method according to claim 16, wherein said laser beam is a wavelength variable laser arbitrarily continuously variable in a predetermined wavelength range, and wherein an incident beam wavelength dependency of the scattering image or the fluorescence image is measured while suitably changing the wavelength.

18. A photoluminescence measuring method according to claim 17, wherein polarization directions of said projected laser beam and of the scattered light or the fluorescence are changed to measure a polarization dependency of the scattering image or the fluorescence image.

19. A photoluminescence measuring method according to claim 18, wherein a transmission center wavelength of the projected laser beam is changed to measure a wavelength dependency of the scattering image or the fluorescence image.

20. A photoluminescence measuring method according to claim 12, wherein a pulse laser is used as said laser beam and wherein a time dependency of the photoluminescence image is measured by measuring the fluorescence generated with the pulse laser with time.

21. A photoluminescence measuring method according to claim 12, wherein said object crystal is a silicon crystal.

22. A photoluminescence measuring method according to claim 21, wherein the wavelength of said projected laser beam is 800 to 1500 nm, and the wavelength of the fluorescence image generated is 0.9 to 2 μm.

* * * * *